United States Patent
Bathe et al.

(10) Patent No.: US 7,229,802 B2
(45) Date of Patent: Jun. 12, 2007

(54) NUCLEOTIDE SEQUENCES CODING FOR THE MTRA AND/OR MTRB PROTEINS

(75) Inventors: Brigitte Bathe, Salzkotten (DE); Natalie Schischka, Bielefeld (DE); Michael Bott, Juelich (DE); Steffen Schaffer, Cologne (DE)

(73) Assignee: Degussa AG, Duesseldorf (DE)

( * ) Notice: Subject to any disclaimer, the term of this patent is extended or adjusted under 35 U.S.C. 154(b) by 283 days.

(21) Appl. No.: 10/651,967

(22) Filed: Sep. 2, 2003

(65) Prior Publication Data

US 2005/0089986 A1 Apr. 28, 2005

Related U.S. Application Data

(62) Division of application No. 09/990,337, filed on Nov. 23, 2001, now Pat. No. 6,703,223.

(30) Foreign Application Priority Data

Nov. 22, 2000 (DE) .................. 100 57 802
May 23, 2001 (DE) .................. 101 25 089

(51) Int. Cl.
- C12P 13/04 (2006.01)
- C12N 9/12 (2006.01)
- C12N 1/20 (2006.01)
- C12N 15/00 (2006.01)
- C07H 21/04 (2006.01)

(52) U.S. Cl. ............... 435/106; 435/115; 435/183; 435/194; 435/252.3; 435/320.1; 536/23.2

(58) Field of Classification Search ............ 435/183, 435/194, 320.1, 106, 115, 252.3; 536/23.2
See application file for complete search history.

(56) References Cited

U.S. PATENT DOCUMENTS

2002/0155554 A1   10/2002   Bathe et al.
2002/0182689 A1   12/2002   Bathe et al.

FOREIGN PATENT DOCUMENTS

EP   1 108 790       6/2001
WO   WO 02/18427    3/2002

OTHER PUBLICATIONS

S.T. Cole, et al., Databae EMBL Online,! pp. 1-11, AC:Z95121, XP-002195723, "Deciphering the Biology of Mycobacterium Tuberculosis from the Complete Genome Sequence," May 6, 1997.
D.C. Saunders, et al., Database EMBL Online,! AC Q9KYW8, pp. 1-2, XP-002195610, "Putative Two-Component System Response Regulator," Oct. 1, 2000.
D.C. Saunders, et al., Database EMBL Online,! AC: Q9KYW9, pp. 1-2, XP-002195612, "Putative Two-Component System Histidine Kinase," Oct. 1, 2000.
L.E. Via, et al., Journal of Bacteriology, vol. 178, No. 11, pp. 3314-3321, XP-002195607, "Elements of Signal Transduction in Mycobacterium Tuberculosis: In Vitro Phosphorylation and in Vivo Expression of the Response Regulator MtrA," Jun. 1996.
M.P. Schmitt, Journal of Bacteriology, vol. 181, No. 17, pp. 5330-5340, XP-002189177, "Identification of a Two-Component Signal Transduction System from Corynebacterium Diphtheriae that Activitates Gene Expression in Response to the Presence of Heme and Hemoglobin," Sep. 1999.
B.J. Eikmanns, et al., Antonie van Leeuwenhoek, vol. 64, No. 2, pp. 145-163, XP-0009185599, "Molecular Aspects of Lysine, Threonine, and Isoleucine Biosyntheses Corynebacterium Glutamicum," 1993.
B. Bathe, et al., Molecular and General Genetics, vol. 252, No. 3, pp. 255-265, XP-000942283, "A physical and Genetic Map of the Corynebacterium Glutamicum ATCC 13032 Chromosome," 1996.
Attwood et al., Which Craft is Best in Bioinformatics? Comput. Chem, 2001, vol. 25(4), pp. 329-339.
Ponting, C.P., Issues in Predicting Protein Function from Sequence, Brief. Bioinform., Mar. 2001, vol. 2(1), pp. 19-29.
Via et al., Accession UO1971, Sep. 11, 1996.

*Primary Examiner*—Tekchand Saidha
*Assistant Examiner*—Christian L. Fronda
(74) *Attorney, Agent, or Firm*—Oblon, Spivak, McClelland, Maier & Neustadt, P.C.

(57) ABSTRACT

The present invention provides nucleotide sequences from *Coryneform* bacteria which code for the MtrA and/or MtrB proteins and processes for the fermentative preparation of amino acids using bacteria in which the mtrA and/or mtrB genes are attenuated.

31 Claims, 2 Drawing Sheets

Figure 1: Plasmid pCR2.1mtrAint
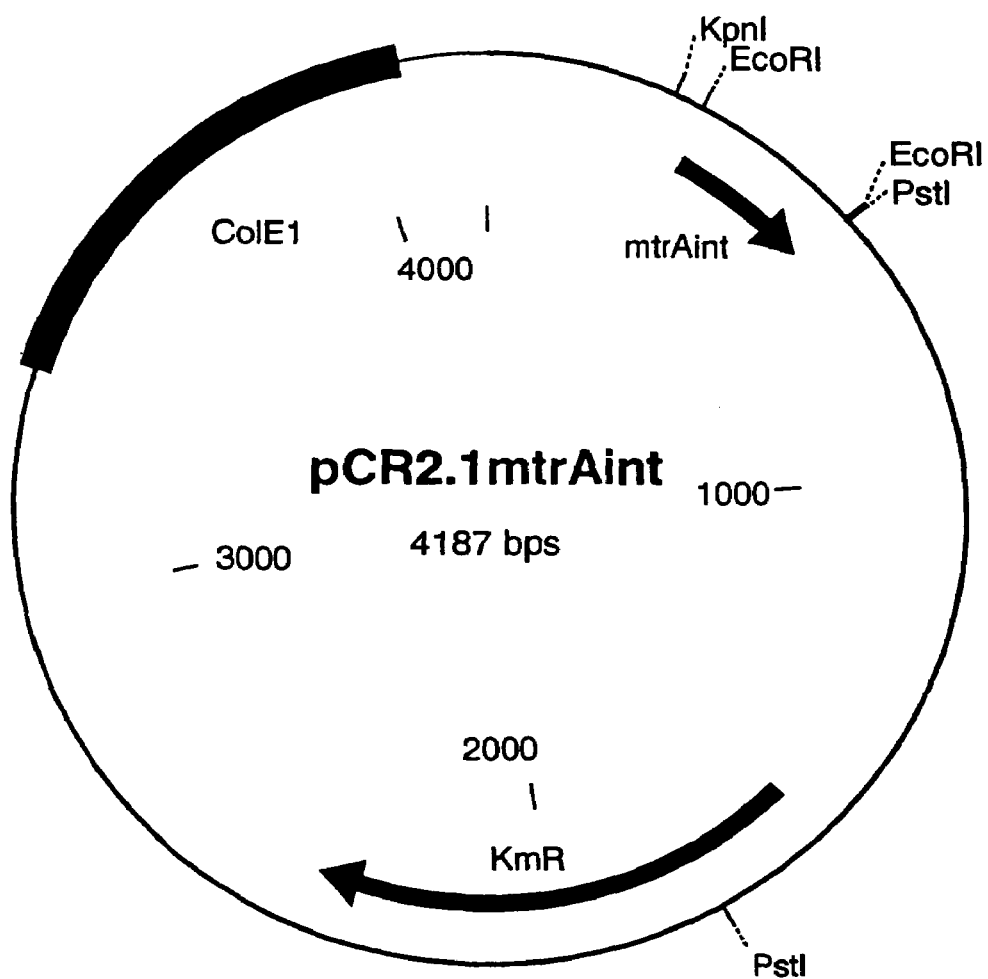

Figure 2: Plasmid pCR2.1mtrBint
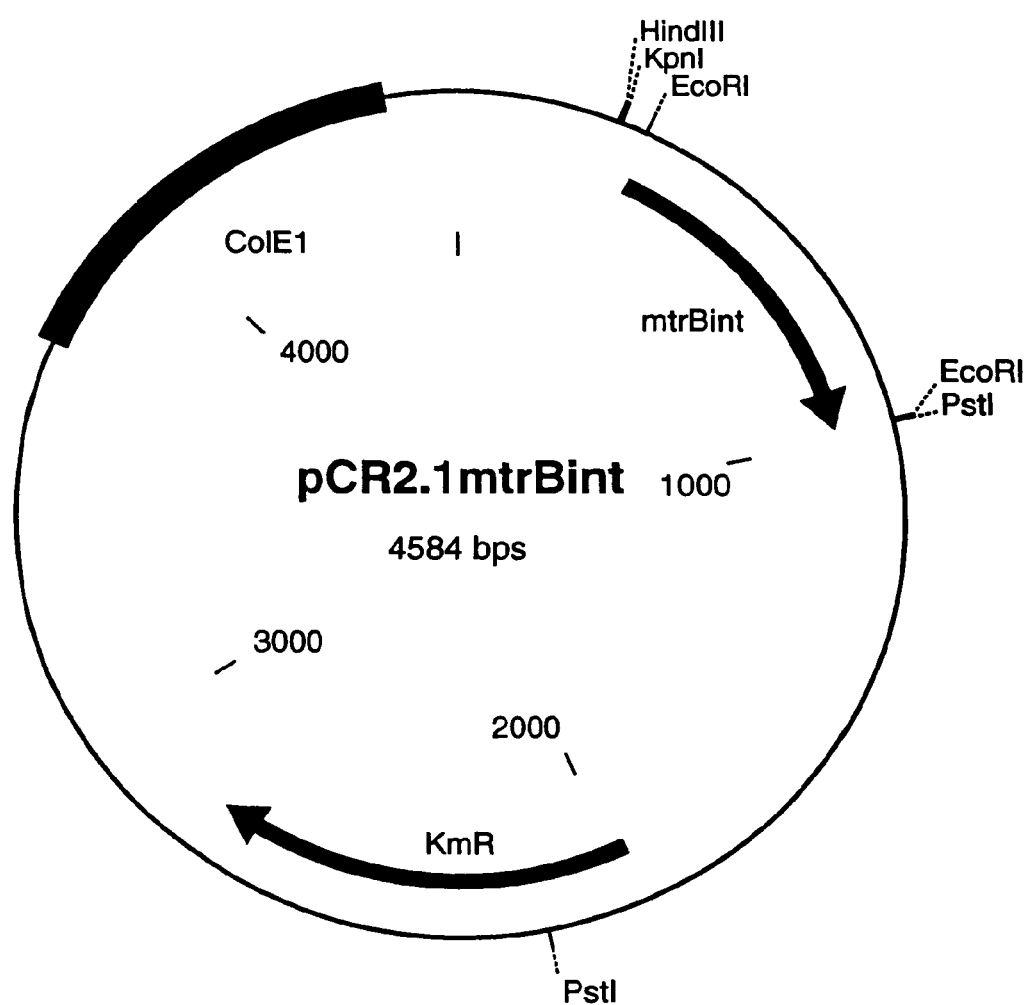

NUCLEOTIDE SEQUENCES CODING FOR THE MTRA AND/OR MTRB PROTEINS

BACKGROUND OF THE INVENTION

1. Field of the Invention

The present invention provides nucleotide sequences from *Coryneform* bacteria which code for the MtrA and/or MtrB proteins and processes for the fermentative preparation of amino acids using bacteria in which the mtrA and/or mtrB genes are attenuated.

2. Discussion of the Background

L-Amino acids, in particular L-lysine, are used in human medicine and in the pharmaceuticals industry, in the foodstuffs industry and very particularly in animal nutrition.

It is known that amino acids are prepared by fermentation from strains of *Coryneform* bacteria, in particular *Corynebacterium glutamicum*. Because of their great importance, work is constantly being undertaken to improve the preparation processes. Improvements to the process can relate to fermentation measures, such as, for example, stirring and supply of oxygen, or the composition of the nutrient media, such as, for example, the sugar concentration during the fermentation, or the working up to the product form by, for example, ion exchange chromatography, or the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and which produce amino acids are obtained in this manner.

Methods of the recombinant DNA technique have also been employed for some years for improving the strain of *Corynebacterium* strains which produce L-amino acid, by amplifying individual amino acid biosynthesis genes and investigating the effect on the amino acid production.

However, there remains a critical need for improved methods of producing L-amino acids and thus for the provision of strains of bacteria producing higher amounts of L-amino acids. On a commercial or industrial scale even small improvements in the yield of L-amino acids, or the efficiency of their production, are economically significant. Prior to the present invention, it was not recognized that attenuating the mtrA and/or mtrB genes encoding response regulator and histidine protein kinase proteins, respectively, would improve L-amino acid yields.

SUMMARY OF THE INVENTION

An object of the present invention is to provide novel measures for the improved production of L-amino acids or amino acid, where these amino acids include L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan, L-arginine and the salts (monohydrochloride or sulfate) thereof.

One object of the present invention is providing a novel process for improving the fermentative production of said L-amino acids, particularly L-lysine. Such a process includes attenuated bacteria, preferably attenuated *Coryneform* bacteria, which express attenuated amounts MtrA and/or MtrB proteins or proteins that have response regulator or histidine protein kinase activities.

Thus, another object of the present invention is providing such a bacterium, which expresses an enhanced amount of the MtrA and/or MtrB proteins or gene products of the mtrA and/or mtrB genes.

Another object of the present invention is providing a bacterium, preferably a *Coryneform* bacterium, which expresses a polypeptide that has an attenuated MtrA response regulator and/or histidine protein kinase activities.

Another object of the invention is to provide a nucleotide sequence encoding a polypeptide having the MtrA and/or MtrB sequences. One embodiment of such a sequence providing both mtrA and mtrB is the nucleotide sequence of SEQ ID NO: 1. Additionally, nucleotides 542 to 1219 of SEQ ID NO:1 comprise the MtrA coding region and nucleotides 1310 to 2818 comprise the MtrB coding region.

A further object of the invention is a method of making proteins or isolated polypeptides having MtrA response regulator and/or histidine protein kinase activities, as well as use of such isolated polypeptides in the production of amino acids. One embodiment of the MtrA polypeptide is the polypeptide having the amino acid sequence of SEQ ID NO: 2. One embodiment of the MtrB polypeptide is the polypeptide having the amino acid sequence of SEQ ID NO:3.

Other objects of the invention include methods of detecting nucleic acid sequences homologous to SEQ ID NO: 1, particularly nucleic acid sequences encoding polypeptides that have MtrA response regulator and/or histidine protein kinase activities, and methods of making nucleic acids encoding such polypeptides.

The above objects highlight certain aspects of the invention. Additional objects, aspects and embodiments of the invention are found in the following detailed description of the invention.

BRIEF DESCRIPTION OF THE DRAWINGS

FIG. 1: Map of the plasmid pCR2.1mtrAint.
FIG. 2: Map of the plasmid pCR2.1mtrBint.

DETAILED DESCRIPTION OF THE INVENTION

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

Reference is made to standard textbooks of molecular biology that contain definitions and methods and means for carrying out basic techniques, encompassed by the present invention. See, for example, Sambrook et al., Molecular Cloning: A Laboratory Manual, Cold Spring Harbor Laboratory, New York (1989), Current Protocols in Molecular Biology, Ausebel et al (eds), John Wiley and Sons, Inc. New York (2000) and the various references cited therein.

"L-amino acids" or "amino acids" as used herein mean one or more amino acids, including their salts, chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-Lysine is particularly preferred.

When L-lysine or lysine are mentioned in the following, not only the bases but also the salts, such as e.g. lysine monohydrochloride or lysine sulfate, are meant by this.

The invention provides an isolated polynucleotide from *Coryneform* bacteria, comprising a polynucleotide sequence which codes for the mtrA gene and/or the mtrB gene, chosen from the group consisting of
a) polynucleotide which is identical to the extent of at least 70% to a polynucleotide which codes for a polypeptide which comprises the amino acid sequence of SEQ ID No. 2,
b) polynucleotide which is identical to the extent of at least 70% to a polynucleotide which codes for a polypeptide which comprises the amino acid sequence of SEQ ID No. 3,
c) polynucleotide which codes for a polypeptide which comprises an amino acid sequence which is identical to the extent of at least 70% to the amino acid sequence of SEQ ID No. 2,
d) polynucleotide which codes for a polypeptide which comprises an amino acid sequence which is identical to the extent of at least 70% to the amino acid sequence of SEQ ID No. 3,
e) polynucleotide which is complementary to the polynucleotides of a), b), c) or d), and
f) polynucleotide comprising at least 15 successive nucleotides of the polynucleotide sequence of a), b), c), d) or e),
the polypeptides preferably having the activity of the response regulator MtrA and/or of the histidine protein kinase MtrB.

The invention also provides the above-mentioned polynucleotides, these preferably being DNAs which are capable of replication, comprising:
(i) the nucleotide sequence, in particular between positions 1 to 2717, shown in SEQ ID No.1, or
(ii) at least one sequence which corresponds to sequence (i) within the degeneracy of the genetic code, or
(iii) at least one sequence which hybridizes with the sequences complementary to sequences (i) or (ii) and optionally
(iv) sense mutations of neutral function in (i) which do not modify the activity of the protein/polypeptide.

Finally, the invention also provides polynucleotides chosen from the group consisting of
a) polynucleotides comprising at least 15 successive nucleotides chosen from the nucleotide sequence of SEQ ID No. 1 between positions 1 and 541,
b) polynucleotides comprising at least 15 successive nucleotides chosen from the nucleotide sequence of SEQ ID No. 1 between positions 542 and 1219,
c) polynucleotides comprising at least 15 successive nucleotides chosen from the nucleotide sequence of SEQ ID No. 1 between positions 1220 and 1309,
d) polynucleotides comprising at least 15 successive nucleotides chosen from the nucleotide sequence of SEQ ID No. 1 between positions 1310 and 2717,
e) polynucleotides comprising at least 15 successive nucleotides chosen from the nucleotide sequence of SEQ ID No. 1 between positions 2718 and 3910.

The invention also provides:
polynucleotides, in particular DNAs, which are capable of replication and comprise the nucleotide sequence as shown in SEQ ID No.1;
polynucleotides which code for polypeptides which comprise the amino acid sequence as shown in SEQ ID No. 2 or SEQ ID No.3;
vectors containing parts of the polynucleotide according to the invention, having at least 15 successive nucleotides of the sequence claimed,
and *Coryneform* bacteria in which the mtrA gene and/or the mtrB gene is attenuated, in particular by an insertion or deletion.

The invention also provides polynucleotides, which substantially comprise a polynucleotide sequence, which are obtainable by screening by means of hybridization of a corresponding gene library of a *Coryneform* bacterium, which comprises the complete gene or parts thereof, with a probe which comprises the sequence of the polynucleotide according to the invention according to SEQ ID No.1 or a fragment thereof, and isolation of the polynucleotide sequence mentioned.

Polynucleotides which comprise the sequences according to the invention are suitable as hybridization probes for RNA, cDNA and DNA, in order to isolate, in the full length, nucleic acids or polynucleotides or genes which code for the response regulator MtrA and/or the histidine protein kinase MtrB, or to isolate those nucleic acids or polynucleotides or genes which have a high similarity with the sequence of the mtrA gene and/or the mtrB gene. Additionally, methods employing DNA chips, microarrays or similar recombinant DNA technology that enables high throughput screening of DNA and polynucleotides which encode the glyceraldehydes 3-phosphate dehydrogenase 2 protein or polynucleotides with homology to the gap2 gene as described herein. Such methods are known in the art and are described, for example, in Current Protocols in Molecular Biology, Ausebel et al (eds), John Wiley and Sons, Inc. New York (2000).

Polynucleotides which comprise the sequences according to the invention are furthermore suitable as primers with the aid of which DNA of genes which code for the response regulator MtrA and/or the histidine protein kinase MtrB can be prepared by the polymerase chain reaction (PCR).

Such oligonucleotides which serve as probes or primers comprise at least 25, 26, 27, 28, 29 or 30, preferably at least 20, 21, 22, 23 or 24, very particularly preferably at least 15, 16, 17, 18 or 19 successive nucleotides. Oligonucleotides with a length of at least 31, 32, 33, 34, 35, 36, 37, 38, 39 or 40 or at least 41, 42, 43, 44, 45, 46, 47, 48, 49 or 50 nucleotides are also suitable. Oligonucleotides with a length of at least 100, 150, 200, 250 or 300 nucleotides are optionally also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

The polynucleotides according to the invention include a polynucleotide according to SEQ ID No. 1 or a fragment prepared therefrom and also those which are at least 70% to 80%, preferably at least 81% to 85%, particularly preferably at least 86% to 90% and very particularly preferably at least 91%, 93%, 95%, 97% or 99% identical to the polynucleotide according to SEQ ID No. 1 or a fragment prepared therefrom.

"Polypeptides" are understood as meaning peptides or proteins which comprise two or more amino acids bonded via peptide bonds.

The polypeptides according to the invention include a polypeptide according to SEQ ID No. 2 and SEQ ID No. 3, in particular those with the biological activity of the response regulator MtrA and the histidine protein kinase MtrB, and also those which are at least 70% to 80%, preferably at least 81% to 85%, particularly preferably at least 86% to 90% and very particularly preferably at least 91%, 93%, 95%, 97% or 99% identical to the polypeptide according to SEQ ID No. 2 and SEQ ID No. 3 and have the activities mentioned.

The invention furthermore relates to a process for the fermentative preparation of amino acids chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine using *Coryneform* bacteria which in particular already produce amino acids and in which the nucleotide sequences which code for the mtrA and/or mtrB gene are attenuated, in particular eliminated or expressed at a low level.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

Preferably, a bacterial strain with attenuated expression of the mtrA and/or mtrB genes encoding a mtrA response regulator or histidine protein kinase will improve amino acid yield at least 1%.

The microorganisms provided by the present invention can prepare amino acids from glucose, sucrose, lactose, fructose, maltose, molasses, starch, cellulose or from glycerol and ethanol. They can be representatives of *Coryneform* bacteria, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum* (*C. glutamicum*), are in particular the known wild-type strains Corynebacterium glutamicum ATCC13032
Corynebacterium acetoglutamicum ATCC15806
Corynebacterium acetoacidophilum ATCC13870
Corynebacterium melassecola ATCC17965
Corynebacterium thermoaminogenes FERM BP-1539
Brevibacterium flavum ATCC14067
Brevibacterium lactofermentum ATCC13869 and
Brevibacterium divaricatum ATCC14020 and L-amino acid-producing mutants or strains prepared therefrom.

The new genes mtrA and mtrB gene of *C. glutamicum* which code for the response regulator MtrA and the histidine protein kinase MtrB have been isolated. The two proteins are part of a two-component system. Two-component regulation systems are distinguished in that various response regulator proteins can be activated by sensor kinases.

To isolate the mtrA gene, the mtrB gene or also other genes of *C. glutamicum*, a gene library of this microorganism is first set up in *Escherichia coli* (*E. coli*). The setting up of gene libraries is described in generally known textbooks and handbooks. The textbook by Winnacker: Gene und Klone, Eine Einführung in die Gentechnologie (Verlag Chemie, Weinheim, Germany, 1990), or the handbook by Sambrook et al.: Molecular Cloning, A Laboratory Manual (Cold Spring Harbor Laboratory Press, 1989) may be mentioned as an example. A well-known gene library is that of the *E. coli* K-12 strain W3110 set up in λ vectors by Kohara et al. (Cell 50, 495–508 (1987)). Bathe et al. (Molecular and General Genetics, 252:255–265, 1996) describe a gene library of *C. glutamicum* ATCC13032, which was set up with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575).

Börmann et al. (Molecular Microbiology 6(3), 317–326)) (1992)) in turn describe a gene library of *C. glutamicum* ATCC13032 using the cosmid pHC79 (Hohn and Collins, 1980, Gene 11, 291–298).

To prepare a gene library of *C. glutamicum* in *E. coli* it is also possible to use plasmids such as pBR322 (Bolivar, 1979, Life Sciences, 25, 807–818) or pUC9 (Vieira et al., 1982, Gene, 19:259–268). Suitable hosts are, in particular, those *E. coli* strains which are restriction- and recombination-defective, such as, for example, the strain DH5αmcr, which has been described by Grant et al. (Proceedings of the National Academy of Sciences USA, 87 (1990) 4645–4649). The long DNA fragments cloned with the aid of cosmids or other λ vectors can then in turn be subcloned and subsequently sequenced in the usual vectors which are suitable for DNA sequencing, such as is described e.g. by Sanger et al. (Proceedings of the National Academy of Sciences of the United States of America, 74:5463–5467, 1977).

The resulting DNA sequences can then be investigated with known algorithms or sequence analysis programs, such as e.g. that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)).

The new DNA sequences of *C. glutamicum* which code for the mtrA and mtrB genes and which, as SEQ ID No. 1, are a constituent of the present invention have been found. The amino acid sequence of the corresponding protein has furthermore been derived from the present DNA sequence by the methods described above. The resulting amino acid sequences of the mtrA and mtrB gene products are shown in SEQ ID No. 2 and SEQ ID No. 3. It is known that enzymes endogenous in the host can split off the N-terminal amino acid methionine or formylmethionine of the protein formed.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. are of neutral function. Such mutations are also called, inter alia, neutral substitutions. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences which result in a corresponding manner from SEQ ID No. 2 are also a constituent of the invention.

In the same way, DNA sequences which hybridize with SEQ ID No. 1 or parts of SEQ ID No. 1 are a constituent of the invention. Finally, DNA sequences which are prepared by the polymerase chain reaction (PCR) using primers which result from SEQ ID No. 1 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) and in Liebl et al. (International Journal of Systematic Bacteriology 41: 255–260 (1991)). The hybridization takes place under stringent conditions, that is to say only hybrids in which the probe and target sequence, i.e. the polynucleotides treated with the probe, are at least 70% identical are formed. It is known that the stringency of the hybridization, including the washing steps, is influenced or determined by varying the buffer composition, the temperature and the salt concentration. The hybridization reaction is preferably carried out under a relatively low stringency compared with the washing steps (Hybaid Hybridisation Guide, Hybaid Limited, Teddington, UK, 1996).

A 5×SSC buffer at a temperature of approx. 50° C.–68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and optionally subsequently 0.5×SSC (The DIG System User's Guide for Filter Hybridisation, Boehringer Mannheim, Mannheim, Germany, 1995) a temperature of approx. 50° C.–68° C. being established. It is optionally possible to lower the salt concentration to 0.1×SSC. Polynucleotide fragments which are, for example, at least 70% or at least 80% or at least 90% to 95% or at least 96% to 99% identical to the sequence of the probe employed can be isolated by increasing the hybridization temperature stepwise from 50° C. to 68° C. in steps of approx. 1–2° C. It is also possible to isolate polynucleotide fragments which are completely identical to the sequence of the probe employed. Further instructions on hybridization are obtainable on the market in the form of so-called kits (e.g. DIG Easy Hyb from Roche Diagnostics GmbH, Mannheim, Germany, Catalogue No. 1603558).

Instructions for amplification of DNA sequences with the aid of the polymerase chain reaction (PCR) can be found by the expert, inter alia, in the handbook by Gait: oligonucleotide Synthesis: A Practical Approach (IRL Press, Oxford, UK, 1984) and in Newton and Graham: PCR (Spektrum Akademischer Verlag, Heidelberg, Germany, 1994).

It has been found that *Coryneform* bacteria produce amino acids in an improved manner after attenuation of the mtrA gene and/or the mtrB gene.

To achieve an attenuation, either the expression of the mtrA gene and/or of the mtrB gene or the catalytic or regulatory properties of the enzyme proteins can be reduced or eliminated. The two measures can optionally be combined.

The reduction in gene expression can take place by suitable culturing or by genetic modification (mutation) of the signal structures of gene expression. Signal structures of gene expression are, for example, repressor genes, activator genes, operators, promoters, attenuators, ribosome binding sites, the start codon and terminators. The expert can find information on this e.g. in the patent application WO 96/15246, in Boyd and Murphy (Journal of Bacteriology 170: 5949 (1988)), in Voskuil and Chambliss (Nucleic Acids Research 26: 3548 (1998), in Jensen and Hammer (Biotechnology and Bioengineering 58: 191 (1998)), in Pátek et al. (Microbiology 142: 1297 (1996)), Vasicova et al. (Journal of Bacteriology 181: 6188 (1999)) and in known textbooks of genetics and molecular biology, such as e.g. the textbook by Knippers ("Molekulare Genetik", 6th edition, Georg Thieme Verlag, Stuttgart, Germany, 1995) or that by Winnacker ("Gene und Klone", VCH Verlagsgesellschaft, Weinheim, Germany, 1990).

Mutations which lead to a change or reduction in the catalytic properties of enzyme proteins are known from the prior art; examples which may be mentioned are the works by Qiu and Goodman (Journal of Biological Chemistry 272: 8611–8617 (1997)), Sugimoto et al. (Bioscience Biotechnology and Biochemistry 61: 1760–1762 (1997)) and Möckel ("Die Threonindehydratase aus *Corynebacterium glutamicum*: Aufhebung der allosterischen Regulation und Struktur des Enzyms", Reports from the Jülich Research Center, Jül-2906, ISSN09442952, Jülich, Germany, 1994). Summarizing descriptions can be found in known textbooks of genetics and molecular biology, such as e.g. that by Hagemann ("Allgemeine Genetik", Gustav Fischer Verlag, Stuttgart, 1986).

Possible mutations are transitions, transversions, insertions and deletions. Depending on the effect of the amino acid exchange on the enzyme activity, "missense mutations" or "nonsense mutations" are referred to. Insertions or deletions of at least one base pair (bp) in a gene lead to frame shift mutations, as a consequence of which incorrect amino acids are incorporated or translation is interrupted prematurely. Deletions of several codons typically lead to a complete loss of the enzyme activity. Instructions on generation of such mutations are prior art and can be found in known textbooks of genetics and molecular biology, such as e.g. the textbook by Knippers ("Molekulare Genetik", 6th edition, Georg Thieme Verlag, Stuttgart, Germany, 1995), that by Winnacker ("Gene und Klone", VCH Verlagsgesellschaft, Weinheim, Germany, 1990) or that by Hagemann ("Allgemeine Genetik", Gustav Fischer Verlag, Stuttgart, 1986).

A common method of mutating genes of *C. glutamicum* is the method of "gene disruption" and "gene replacement" described by Schwarzer and Pühler (Bio/Technology 9, 84–87 (1991)).

In the method of gene disruption a central part of the coding region of the gene of interest is cloned in a plasmid vector which can replicate in a host (typically *E. coli*), but not in *C. glutamicum*. Possible vectors are, for example, pSUP301 (Simon et al., Bio/Technology 1, 784–791 (1983)), pK18mob or pK19mob (Schäfer et al., Gene 145, 69–73 (1994)), pK18mobsacB or pK19mobsacB (Jäger et al., Journal of Bacteriology 174: 5462–65 (1992)), pGEM-T (Promega Corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, Holland; Bernard et al., Journal of Molecular Biology, 234: 534–541 (1993)) or pEMI (Schrumpf et al, 1991, Journal of Bacteriology 173:4510–4516). The plasmid vector which contains the central part of the coding region of the gene is then transferred into the desired strain of *C. glutamicum* by conjugation or transformation. The method of conjugation is described, for example, by Schäfer et al. (Applied and Environmental Microbiology 60, 756–759 (1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross-over" event, the coding region of the gene in question is interrupted by the vector sequence and two incomplete alleles are obtained, one lacking the 3' end and one lacking the 5' end. This method has been used, for example, by Fitzpatrick et al. (Applied Microbiology and Biotechnology 42, 575–580 (1994)) to eliminate the recA gene of C. glutamicum.

In the method of "gene replacement", a mutation, such as e.g. a deletion, insertion or base exchange, is established in vitro in the gene of interest. The allele prepared is in turn cloned in a vector which is not replicative for C. glutamicum and this is then transferred into the desired host of C. glutamicum by transformation or conjugation. After homologous recombination by means of a first "cross-over" event which effects integration and a suitable second "cross-over" event which effects excision in the target gene or in the target sequence, the incorporation of the mutation or of the allele is achieved. This method was used, for example, by Peters-Wendisch et al. (Microbiology 144, 915–927 (1998)) to eliminate the pyc gene of C. glutamicum by a deletion.

A deletion, insertion or a base exchange can be incorporated into the mtrA gene and/or the mtrB gene in this manner.

In addition, it may be advantageous for the production of L-amino acids to enhance, in particular over-express, one or more enzymes of the particular biosynthesis pathway, of glycolysis, of anaplerosis, of the citric acid cycle, of the pentose phosphate cycle, of amino acid export and optionally regulatory proteins, in addition to the attenuation of the mtrA gene and/or mtrB gene.

The term "enhancement" in this connection describes the increase in the intracellular activity of one or more enzymes (proteins) in a microorganism which are coded by the corresponding DNA, for example by increasing the number of copies of the gene or genes, using a potent promoter or using a gene or allele which codes for a corresponding enzyme (protein) having a high activity, and optionally combining these measures.

By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on that of the wild-type protein or the activity or concentration of the protein in the starting microorganism.

Thus, for the preparation of L-amino acids, in addition to the attenuation of the mtrA gene and/or the mtrB gene at the same time one or more of the genes chosen from the group consisting of the dapA gene which codes for dihydrodipicolinate synthase (EP-B 0 197 335),
the gap gene which codes for glyceraldehyde 3-phosphate dehydrogenase (Eikmanns (1992), Journal of Bacteriology 174:6076–6086),
the tpi gene which codes for triose phosphate isomerase (Eikmanns (1992), Journal of Bacteriology 174:6076–6086),
the pgk gene which codes for 3-phosphoglycerate kinase (Eikmanns (1992), Journal of Bacteriology 174:6076–6086), the zwf gene which codes for glucose 6-phosphate dehydrogenase (JP-A-09224661),
the pyc gene which codes for pyruvate carboxylase (DE-A-198 31 609),
the mqo gene which codes for malate-quinone oxidoreductase (Molenaar et al., European Journal of Biochemistry 254, 395–403 (1998)),
the lysC gene which codes for a feed-back resistant aspartate kinase (Accession No.P26512; EP-B-0387527; EP-A-0699759; WO 00/63388),
the lysE gene which codes for lysine export (DE-A-195 48 222),
the hom gene which codes for homoserine dehydrogenase (EP-A 0131171),
the ilvA gene which codes for threonine dehydratase (Möckel et al., Journal of Bacteriology (1992) 8065–8072)) or the ilvA(Fbr) allele which codes for a "feed back resistant" threonine dehydratase (Möckel et al., (1994) Molecular Microbiology 13: 833–842),
the ilvBN gene which codes for acetohydroxy-acid synthase (EP-B 0356739),
the ilvD gene which codes for dihydroxy-acid dehydratase (Sahm and Eggeling (1999) Applied and Environmental Microbiology 65: 1973–1979),
the zwa1 gene which codes for the Zwa1 protein (DE: 19959328.0, DSM 13115)
can be enhanced, in particular over-expressed.

It may furthermore be advantageous for the production of amino acids, in addition to the attenuation of the mtrA gene and/or the mtrB gene, at the same time for one or more of the genes chosen from the group consisting of the pck gene which codes for phosphoenol pyruvate carboxykinase (DE 199 50 409.1, DSM 13047),
the pgi gene which codes for glucose 6-phosphate isomerase (U.S. Ser. No. 09/396,478, DSM 12969),
the poxB gene which codes for pyruvate oxidase (DE: 1995 1975.7, DSM 13114),
the zwa2 gene which codes for the Zwa2 protein (DE: 19959327.2, DSM 13113)
to be attenuated, in particular for the expression thereof to be reduced.

In addition to the attenuation of the mtrA gene and/or the mtrB gene it may furthermore be advantageous for the production of amino acids to eliminate undesirable side reactions (Nakayama: "Breeding of Amino Acid Producing Microorganisms", in: Overproduction of Microbial Products, Krumphanzl, Sikyta, Vanek (eds.), Academic Press, London, UK, 1982).

The invention also provides the microorganisms prepared according to the invention, and these can be cultured continuously or discontinuously in the batch process (batch culture) or in the fed batch (feed process) or repeated fed batch process (repetitive feed process) for the purpose of production of L-amino acids. A summary of known culture methods is described in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Sugars and carbohydrates, such as e.g. glucose, sucrose, lactose, fructose, maltose, molasses, starch and cellulose, oils and fats, such as, for example, soya oil, sunflower oil, groundnut oil and coconut fat, fatty acids, such as, for example, palmitic acid, stearic acid and linoleic acid, alcohols, such as, for example, glycerol and ethanol, and organic acids, such as, for example, acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as, for example, magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as, for example, fatty acid polyglycol esters, can be employed to control the development of foam. Suitable substances having a selective action, such as, for example, antibiotics, can be added to the medium to maintain the stability of plasmids. To maintain aerobic conditions, oxygen or oxygen-containing gas mixtures, such as, for example, air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

Methods for the determination of L-amino acids are known from the prior art. The analysis can thus be carried out, for example, as described by Spackman et al. (Analytical Chemistry, 30, (1958), 1190) by anion exchange chromatography with subsequent ninhydrin derivation, or it can be carried out by reversed phase HPLC, for example as described by Lindroth et al. (Analytical Chemistry (1979) 51: 1167–1174).

The process according to the invention is used for fermentative preparation of amino acids.

The following microorganisms were deposited as a pure culture on 11th Apr. 2001 at the Deutsche Sammlung für Mikroorganismen und Zellkulturen (DSMZ=German Collection of Microorganisms and Cell Cultures, Braunschweig, Germany) in accordance with the Budapest Treaty:

*Escherichia coli* Top10/pCR2.1mtrAint as DSM 14227,
*Escherichia coli* Top10/pCR2.1mtrBint as DSM 14228.

The present invention is explained in more detail in the following with the aid of embodiment examples.

The isolation of plasmid DNA from *Escherichia coli* and all techniques of restriction, Klenow and alkaline phosphatase treatment were carried out by the method of Sambrook et al. (Molecular Cloning. A Laboratory Manual, 1989, Cold Spring Harbor Laboratory Press, Cold Spring Harbor, N.Y., USA). Methods for transformation of *Escherichia coli* are also described in this handbook.

The composition of the usual nutrient media, such as LB or TY medium, can also be found in the handbook by Sambrook et al.

Having generally described this invention, a further understanding can be obtained by reference to certain specific examples which are provided herein for purposes of illustration only, and are not intended to be limiting unless otherwise specified.

EXAMPLE 1

Preparation of a Genomic Cosmid Gene Library from *C. glutamicum* ATCC 13032

Chromosomal DNA from *C. glutamicum* ATCC 13032 is isolated as described by Tauch et al. (1995, Plasmid 33:168–179) and partly cleaved with the restriction enzyme Sau3AI (Amersham Pharmacia, Freiburg, Germany, Product Description Sau3AI, Code no. 27-0913-02). The DNA fragments are dephosphorylated with shrimp alkaline phosphatase (Roche Molecular Biochemicals, Mannheim, Germany, Product Description SAP, Code no. 1758250). The DNA of the cosmid vector SuperCos1 (Wahl et al. (1987), Proceedings of the National Academy of Sciences, USA 84:2160–2164), obtained from Stratagene (La Jolla, USA, Product Description SuperCos1 Cosmid Vector Kit, Code no. 251301) is cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA is then cleaved with the restriction enzyme BamHI (Amersham Pharmacia, Freiburg, Germany, Product Description BamHI, Code no. 27-0868-04). The cosmid DNA treated in this manner is mixed with the treated ATCC13032 DNA and the batch is treated with T4 DNA ligase (Amersham Pharmacia, Freiburg, Germany, Product Description T4-DNA-Ligase, Code no.27-0870-04). The ligation mixture is then packed in phages with the aid of Gigapack II XL Packing Extract (Stratagene, La Jolla, USA, Product Description Gigapack II XL Packing Extract, Code no. 200217).

For infection of the *E. coli* strain NM554 (Raleigh et al. 1988, Nucleic Acids Res. 16:1563–1575) the cells are taken up in 10 mM MgSO$_4$ and mixed with an aliquot of the phage suspension. The infection and titering of the cosmid library are carried out as described by Sambrook et al. (1989, Molecular Cloning: A Laboratory Manual, Cold Spring Harbor), the cells being plated out on LB agar (Lennox, 1955, Virology, 1:190)+100 mg/l ampicillin. After incubation overnight at 37° C., recombinant individual clones are selected.

EXAMPLE 2

Isolation and Sequencing of the mtrA and mtrB Genes

The cosmid DNA of an individual colony is isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments are dephosphorylated with shrimp alkaline phosphatase (Roche Molecular Biochemicals, Mannheim, Germany, Product Description SAP, Product No. 1758250). After separation by gel electrophoresis, the cosmid fragments in the size range of 1500 to 2000 bp are isolated with the QiaExII Gel Extraction Kit (Product No. 20021, Qiagen, Hilden, Germany).

The DNA of the sequencing vector pZero-1, obtained from Invitrogen (Groningen, The Netherlands, Product Description Zero Background Cloning Kit, Product No. K2500-01) is cleaved with the restriction enzyme BamHI (Amersham Pharmacia, Freiburg, Germany, Product Description BamHI, Product No. 27-0868-04). The ligation of the cosmid fragments in the sequencing vector pZero-1 is carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture is then electroporated (Tauch et al. 1994, FEMS Microbiol. Letters, 123:343–7) into the *E. coli* strain DH5αmcr (Grant, 1990, Proceedings of the National Academy of Sciences, U.S.A., 87:4645–4649). Letters, 123:343–7) and plated out on LB agar (Lennox, 1955, Virology, 1:190) with 50 mg/l zeocin.

The plasmid preparation of the recombinant clones is carried out with a Biorobot 9600 (Product No. 900200, Qiagen, Hilden, Germany). The sequencing is carried out by the dideoxy chain-stopping method of Sanger et al. (1977, Proceedings of the National Academies of Sciences, U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The separation by gel electrophoresis and analysis of the sequencing reaction are carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained are then processed using the Staden program package (1986, Nucleic Acids Research, 14:217–231) version 97-0. The individual sequences of the pZero1 derivatives are assembled to a continuous contig. The computer-assisted coding region analysis is prepared with the XNIP program (Staden, 1986, Nucleic Acids Research 14:217–231). Further analyses are carried out with the "BLAST search program" (Altschul et al., 1997, Nucleic Acids Research, 25:3389–3402) against the non-redundant databank of the "National Center for Biotechnology Information" (NCBI, Bethesda, Md., USA).

The resulting nucleotide sequence is shown in SEQ ID No. 1. Analysis of the nucleotide sequence shows two open reading frames of 681 base pairs and 1512 base pairs, which are called the mtrA gene and mtrB gene. The mtrA gene codes for a polypeptide of 226 amino acids. The mtrB gene codes for a polypeptide of 503 amino acids.

EXAMPLE 3

Preparation of Integration Vectors for Integration Mutagenesis of the mtrA and mtrB Genes From the strain ATCC 13032, chromosomal DNA is isolated by the method of Eikmanns et al. (Microbiology 140: 1817–1828 (1994)). On the basis of the sequence of the mtrA and mtrB genes known for *C. glutamicum* from Example 2, the following oligonucleotides are chosen for the polymerase chain reaction (SEQ ID NOS:4, 5, 6, and 7):

mtrA-int1:
5' TGA TGC TTC CAG GCA TGA AC 3'
mtrA-int2:
5' GAT CGC CGA CTT CGA TGA TT 3'
mtrB-int1:
5' ACG ATG ACC TGG TGG TCT CT 3'
mtrB-int2:
5' GAC TCG AAT CGG TCC AAC TC 3'

The primers shown are synthesized by MWG Biotech (Ebersberg, Germany) and the PCR reaction is carried out by the standard PCR method of Innis et al. (PCR Protocols. A Guide to Methods and Applications, 1990, Academic Press) with the Taq-polymerase from Boehringer Mannheim (Germany, Product Description Taq DNA polymerase, Product No. 1 146 165). With the aid of the polymerase chain reaction, the primers allow amplification of an internal fragment of the mtrA gene 237 bp in size and of an internal fragment of the mtrB gene 634 bp in size. The products amplified in this way are tested electrophoretically in a 0.8% agarose gel.

The amplified DNA fragments are ligated with the TOPO TA Cloning Kit from Invitrogen Corporation (Carlsbad, Calif., USA; Catalogue Number K4500-01) in each case in the vector pCR2.1-TOPO (Mead at al. (1991) Bio/Technology 9:657–663).

The *E. coli* strain TOP10 is then electroporated with the ligation batches (Hanahan, In: DNA cloning. A Practical Approach. Vol. I, IRL-Press, Oxford, Washington D.C., USA, 1985). Selection for plasmid-carrying cells is made by plating out the transformation batch on LB agar (Sambrook et al., Molecular Cloning: A Laboratory Manual. $2^{nd}$ Ed., Cold Spring Harbor Laboratory Press, Cold Spring Harbor, N.Y., 1989), which has been supplemented with 50 mg/l kanamycin. Plasmid DNA is isolated from in each case a transformant with the aid of the QIAprep Spin Miniprep Kit from Qiagen and checked by restriction with the restriction enzyme EcoRI and subsequent agarose gel electrophoresis (0.8%). The plasmids are called pCR2.1mtrAint and pCR2.1mtrBint and are shown in FIG. 1 and in FIG. 2.

EXAMPLE 4

Integration Mutagenesis of the mtrA Gene in the Strain DSM 5715

The vector pCR2.1mtrAint mentioned in Example 3 is electroporated by the electroporation method of Tauch et al. (FEMS Microbiological Letters, 123:343–347 (1994)) in *Corynebacterium glutamicum* DSM 5715. The strain DSM 5715 is an AEC-resistant lysine producer. The vector pCR2.1mtrAint cannot replicate independently in DSM5715 and is retained in the cell only if it has integrated into the chromosome of DSM 5715. Selection of clones with pCR2.1mtrAint integrated into the chromosome is carried out by plating out the electroporation batch on LB agar (Sambrook et al., Molecular Cloning: A Laboratory Manual. $2^{nd}$ Ed., Cold Spring Harbor Laboratory Press, Cold Spring Harbor, N.Y.), which has been supplemented with 15 mg/l kanamycin.

For detection of the integration, the mtrAint fragment is labeled with the Dig hybridization kit from Boehringer by the method of "The DIG System Users Guide for Filter Hybridization" of Boehringer Mannheim GmbH (Mannheim, Germany, 1993). Chromosomal DNA of a potential integrant is isolated by the method of Eikmanns et al. (Microbiology 140: 1817–1828 (1994)) and in each case cleaved with the restriction enzymes KpnI, EcoRI and PstI. The fragments formed are separated by means of agarose gel electrophoresis and hybridized at 68° C. with the Dig hybridization kit from Boehringer. The plasmid pCR2.1mtrAint mentioned in Example 3 has been inserted into the chromosome of DSM5715 within the chromosomal mtrA gene. The strain is called DSM5715::pCR2.1mtrAint.

EXAMPLE 5

Integration Mutagenesis of the mtrB Gene in the Strain DSM 5715

The vector pCR2.1mtrBint mentioned in Example 3 is electroporated by the electroporation method of Tauch et al. (FEMS Microbiological Letters, 123:343–347 (1994)) in *Corynebacterium glutamicum* DSM 5715. The strain DSM 5715 is an AEC-resistant lysine producer. The vector pCR2.1mtrBint cannot replicate independently in DSM5715 and is retained in the cell only if it has integrated into the chromosome of DSM 5715. Selection of clones with pCR2.1mtrBint integrated into the chromosome is carried out by plating out the electroporation batch on LB agar (Sambrook et al., Molecular Cloning: A Laboratory Manual. $2^{nd}$ Ed., Cold Spring Harbor Laboratory Press, Cold Spring Harbor, N.Y.), which has been supplemented with 15 mg/l kanamycin.

For detection of the integration, the mtrBint fragment is labeled with the Dig hybridization kit from Boehringer by the method of "The DIG System Users Guide for Filter Hybridization" of Boehringer Mannheim GmbH (Mannheim, Germany, 1993). Chromosomal DNA of a potential integrant is isolated by the method of Eikmanns et al. (Microbiology 140: 1817–1828 (1994)) and in each case cleaved with the restriction enzymes KpnI, EcoRI and PstI. The fragments formed are separated by means of agarose gel electrophoresis and hybridized at 68° C. with the Dig hybridization kit from Boehringer. The plasmid pCR2.1mtrBint mentioned in Example 3 has been inserted into the chromosome of DSM5715 within the chromosomal mtrB gene. The strain is called DSM5715::pCR2.1mtrBint.

EXAMPLE 6

Preparation of lysine

The *C. glutamicum* strain DSM5715::pCR2.1mtrBint obtained in Example 5 is cultured in a nutrient medium suitable for the production of lysine and the lysine content in the culture supernatant is determined.

For this, the strain is first incubated on an agar plate with the corresponding antibiotic (brain-heart agar with kanamycin 25 mg/l) for 24 hours at 33° C. Starting from this agar plate culture, a preculture is seeded (10 ml medium in a 100 ml conical flask). The complete medium Cg III is used as the medium for the preculture.

| Medium Cg III | |
|---|---|
| NaCl | 2.5 g/l |
| Bacto-Peptone | 10 g/l |
| Bacto-Yeast extract | 10 g/l |
| Glucose (autoclaved separately) | 2% (w/v) |

The pH is brought to pH 7.4

Kanamycin (25 mg/l) is added to this. The preculture is incubated for 16 hours at 33° C. at 240 rpm on a shaking machine. A main culture us seeded from this preculture such that the initial OD (660 nm) of the main culture is 0.1. Medium MM is used for the main culture.

| Medium MM | |
|---|---|
| CSL (corn steep liquor) | 5 g/l |
| MOPS (morpholinopropanesulfonic acid) | 20 g/l |
| Glucose (autoclaved separately) | 50 g/l |

| -continued | |
|---|---|
| Medium MM | |
| Salts: | |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| Leucine (sterile-filtered) | 0.1 g/l |
| $CaCO_3$ | 25 g/l |

The CSL, MOPS and the salt solution are brought to pH 7 with aqueous ammonia and autoclaved. The sterile substrate and vitamin solutions are then added, and the $CaCO_3$ autoclaved in the dry state is added.

Culturing is carried out in a 10 ml volume in 100 ml conical flasks with baffles. Kanamycin (25 mg/l) was added. Culturing is carried out at 33° C. and 80% atmospheric humidity.

After 72 hours, the OD is determined at a measurement wavelength of 660 nm with a Biomek 1000 (Beckmann Instruments GmbH, Munich). The amount of lysine formed is determined with an amino acid analyzer from Eppendorf-BioTronik (Hamburg, Germany) by ion exchange chromatography and post-column derivation with ninhydrin detection.

The result of the experiment is shown in Table 1.

TABLE 1

| Strain | OD (660 nm) | Lysine HCl g/l |
|---|---|---|
| DSM5715 | 12.2 | 13.59 |
| DSM5715::pCR2.1mtrBint | 11.9 | 14.54 |

The abbreviations and designations used have the following meaning.

KMR: Kanamycin resistance gene

KpnI: Cleavage site of the restriction enzyme KpnI

EcoRI: Cleavage site of the restriction enzyme EcoRI

PstI: Cleavage site of the restriction enzyme PstI mtrAint: Internal fragment of the mtrA gene mtrBint: Internal fragment of the mtrb gene ColE1: Replication origin of the plasmid ColE1

The present application claims priority to German Application No. DE 10057802.0, which was filed on Nov. 11, 2001 and German Application No. DE 10125089.4, which was filed on may 23, 2001; the entire contents of both documents are incorporated herein by reference.

Obviously, numerous modifications and variations on the present invention are possible in light of the above teachings. It is therefore to be understood that within the scope of the appended claims, the invention may be practiced otherwise than as specifically described herein.

What is claimed is:

1. An isolated *coryneform* bacterium, which comprises an attenuated polynucleotide encoding a histidine protein kinase, wherein said polynucleotide comprises, prior to said attenuation, a sequence that is at least 95% identical to nucleotides 1310–2818 of SEQ ID NO: 1.

2. The isolated *coryneform* bacterium of claim 1, wherein said polynucleotide comprises a sequence that is at least 97% identical to nucleotides 1310 to 2818 of SEQ ID NO:1.

3. The isolated *coryneform* bacterium of claim 1, wherein said polynucleotide comprises a nucleotide sequence that hybridizes under stringent conditions to a polynucleotide that is complimentary to nucleotides 1310 to 2818 of SEQ ID NO:1, wherein said stringent conditions comprise washing in 0.5×SSC at a temperature of 68° C. and wherein said hybridization is performed in 5×SSC at a temperature of 68° C. and wherein said polynucleotide encoding a histidine protein kinase.

4. *Escherichia coli* DSM 14228.

5. A process for producing L-amino acids comprising culturing a bacterial cell in a medium suitable for producing L-amino acids, wherein said bacterial cell comprises an attenuated polynucleotide encoding a histidine protein kinase, wherein said polynucleotide comprises, prior to said attenuation, a sequence that is at least 95% identical to nucleotides 1310–2818 of SEQ ID NO: 1.

6. The process of claim 5, wherein said bacterial cell is a *Corynebacterium* or *Brevibacterium*.

7. The process of claim 6, wherein said bacterial cell is selected from the group consisting of *Corynebacterium glutamicum, Corynebacterium acetoglutamicum, Corynebacterium acetoacidophilum, Corynebacterium melassecola, Corynebacterium thermoaminogenes, Brevibacterium flavum, Brevibacterium lactofermentum*, and *Brevibacterium divaricatum*.

8. The process of claim 5, wherein said polynucleotide comprises the nucleotides 1310 to 2818 of SEQ ID NO:1.

9. The process of claim 5, wherein said polynucleotide comprises a nucleotide sequence that hybridizes under stringent conditions to a polynucleotide that is complimentary to nucleotides 1310 to 2818 of SEQ ID NO:1, wherein said stringent conditions comprise washing in 0.5×SSC at a temperature of 68° C. and wherein said hybridization is performed in 5×SSC at a temperature of 68° C. and wherein said polynucleotide encoding a histidine protein kinase.

10. The process of claim 5, wherein said L-amino acid is L-lysine.

11. The process of claim 5, wherein said bacteria further comprises at least one polynucleotide whose expression is enhanced, wherein said polynucleotide encodes an enzyme encoded by a polynucleotide selected from the group consisting of dapA, gap, tpl, pgk, zwf pyc, mqo, lysC, lysE, hom, ilvA, ilvBN, ilvD and zwa1.

12. The process of claim 5, wherein said bacteria further comprises at least one polynucleotide whose expression is attenuated, wherein said polynucleotide encodes an enzyme encoded by a polynucleotide selected from the group consisting of pck, pgi, poxB, and zwa2.

13. The isolated *Coryneform* bacterium of claim 1, wherein said polynucleotide comprises a sequence that is at least 99% identical to nucleotides 1310 to 2818 of SEQ ID NO:1.

14. The isolated *coryneform* bacterium of claim 3, wherein said stringent conditions comprise washing in 0.1× SSC at a temperature of 68° C.

15. The isolated *coryneform* bacterium of claim 3, wherein said attenuation is achieved by elimination of the intracellular activity of protein encoded by said polynucleotide.

16. A process for producing L-lysine comprising culturing a *coryneform* bacterium according to claim 3 in a medium suitable for producing L-lysine.

17. The process of claim 16, wherein said bacterial cell is a *Corynebacterium* or *Brevibacterium*.

18. The process of claim 17, wherein said bacterial cell is selected from the group consisting of *Corynebacterium glutamicum, Corynebacterium acetoglutamicum, Corynebacterium acetoacidophilum, Corynebacterium melassecola, Corynebacterium thermoaminogenes, Brevibacterium flavum, Brevibacterium lactofermentum*, and *Brevibacterium divaricatum*.

19. The process of claim 16, wherein said bacteria further comprises a polynucleotide whose expression is attenuated and said polynucleotide comprises a sequence that is at least 95% homologous to nucleotides 542 to 1219 of SEQ ID NO:1.

20. The process of claim 16, wherein said bacteria further comprises at least one polynucleotide whose expression is attenuated, wherein said polynucleotide encodes an enzyme encoded by a polynucleotide selected from the group consisting of dapA, gap, tpl, pgk, zwf pyc, mqo, lysC, lysE, hom, ilvA, ilvBN, ilvD and zwa 1.

21. The process of claim 16, wherein said bacteria further comprises at least one polynucleotide whose expression is attenuated, wherein said polynucleotide encodes an enzyme encoded by a polynucleotide selected from the group consisting of pck, pgi, poxB, arid zwa2.

22. An isolated *coryneform* bacterium, which comprises an attenuated polynucleotide encoding a histidine protein kinase, wherein said histidine protein kinase, prior to said attenuation, comprises an amino acid sequence that is at least 95% identical to SEQ ID NO: 3.

23. The isolated *coryneform* bacterium of claim 22, wherein said histidine protein kinsase comprises an amino acid sequence that is at least 97% identical to SEQ ID NO: 3.

24. The isolated *coryneform* bacterium of claim 22, wherein said histidine protein kinsase comprises an amino acid sequence that is at least 99% identical to SEQ ID NO: 3.

25. The isolated *coryneform* bacterium of claim 22, wherein said attenuation is achieved by elimination of the intracellular activity of protein encoded by said polynucleotide.

26. A process for producing L-lysine comprising culturing a *coryneform* bacterium according to claim 22 in a medium suitable for producing L-lysine.

27. The process of claim 26, wherein said bacterial cell is a *Corynebacterium* or *Brevibacterium*.

28. The process of claim 27, wherein said bacterial cell is selected from the group consisting of *Corynebacterium glutamicum, Corynebacterium acetoglutamicum, Corynebacterium acetoacidophilum, Corynebacterium melassecola, Corynebacterium thermoaminogenes, Brevibacterium flavum, Brevibacterium lactofermentum*, and *Brevibacterium divaricatum*.

29. The process of claim 26, wherein said bacteria further comprises a polynucleotide whose expression is attenuated and said polynucleotide comprises a sequence that is at least 95% homologous to nucleotides 542 to 1219 of SEQ ID NO:1.

30. The process of claim 26, wherein said bacteria further comprises at least one polynucleotide whose expression is attenuated, wherein said polynucleotide encodes an enzyme encoded by a polynucleotide selected from the group consisting of dapA, gap, tpl, pgk, zwf pyc, mqo, lysC, lysE, hom, ilvA, ilvBN, ilvD and zwa 1.

31. The process of claim 26, wherein said bacteria further comprises at least one polynucleotide whose expression is attenuated, wherein said polynucleotide encodes an enzyme encoded by a polynucleotide selected from the group consisting of pck, pgi, poxB, and zwa2.

* * * * *

SEQUENCE LISTING

<160> NUMBER OF SEQ ID NOS: 7

<210> SEQ ID NO 1
<211> LENGTH: 3910
<212> TYPE: DNA
<213> ORGANISM: Corynebacterium glutamicum
<220> FEATURE:
<221> NAME/KEY: CDS
<222> LOCATION: (542)..(1219)
<223> OTHER INFORMATION:
<220> FEATURE:
<221> NAME/KEY: CDS
<222> LOCATION: (1310)..(2818)
<223> OTHER INFORMATION:

<400> SEQUENCE: 1

```
acgttatgaa acctcgattc acgcccaatt ggccgcggaa gcactccacg gccgcatggg      60
cgacctcacc gacagcgcct acgccatggc cacgcttttc gccctcgacc gccacttcgc     120
gattgatgac ttaaatgcgc cggcgtggt gctgctcgac cgatacgtcg cctccaacgc      180
ggcttatacc gccgccagat tgcttgacga cgacgccccc cgctgggttg ccgacctgga     240
attcgggcgg cttgggctcc cacgtccgac gcttcaagtg ttgttggata ccccgcgga     300 ggtagcgcaa gatagggcta gacgtcgaga gcgcttgac tccgcgcgtg cgcgggaccg     360
ctatgaatcg gattcggcgc tgcagcaacg caccgccgag cactatcgcc gcctcgcggc     420
ggacaactgg gaatcaccgt ggatcgtggt tgcccctgat gaagaccccg gccacgttgc     480
gcagagaatc gtggaattcc tgggtactat aaactaatcc caattagcag gaaggattct     540
```

| Codon | AA | Pos | Num |
|---|---|---|---|
| c atg tca cag aaa att ctc gtg gtt gat gat gat ccc gcc atc tcc gag | Met Ser Gln Lys Ile Leu Val Val Asp Asp Asp Pro Ala Ile Ser Glu | 1 5 10 15 | 589 |
| atg ctc acc atc gtg ctc agc gca gaa ggc ttt gac acc gta gct gtc | Met Leu Thr Ile Val Leu Ser Ala Glu Gly Phe Asp Thr Val Ala Val | 20 25 30 | 637 |
| acc gac ggc gca ctc gcc gtg gaa acc gcc tcc cgg gaa caa ccg gat | Thr Asp Gly Ala Leu Ala Val Glu Thr Ala Ser Arg Glu Gln Pro Asp | 35 40 45 | 685 |
| ctg att ttg ctc gac ttg atg ctt cca ggc atg aac ggc atc gac att | Leu Ile Leu Leu Asp Leu Met Leu Pro Gly Met Asn Gly Ile Asp Ile | 50 55 60 | 733 |
| tgt cgc ctc atc cgc caa gaa tcc tcc gta ccc atc atc atg ctc acc | Cys Arg Leu Ile Arg Gln Glu Ser Ser Val Pro Ile Ile Met Leu Thr | 65 70 75 80 | 781 |
| gcc aaa acc gac acc gtt gat gtg gtg ctc ggt ttg gaa tcc ggt gca | Ala Lys Thr Asp Thr Val Asp Val Val Leu Gly Leu Glu Ser Gly Ala | 85 90 95 | 829 |
| gac gat tac gtg aac aag cct ttc aaa gcg aaa gaa ctt gtc gcc cgc | Asp Asp Tyr Val Asn Lys Pro Phe Lys Ala Lys Glu Leu Val Ala Arg | 100 105 110 | 877 |
| atc cgt gcc cgc ctc cgc gca acc gtg gac gag ccc agc gaa atc atc | Ile Arg Ala Arg Leu Arg Ala Thr Val Asp Glu Pro Ser Glu Ile Ile | 115 120 125 | 925 |
| gaa gtc ggc gat ctg tcc atc gac gtc cca gca cac acc gtc aaa cga | Glu Val Gly Asp Leu Ser Ile Asp Val Pro Ala His Thr Val Lys Arg | 130 135 140 | 973 |
| aac ggc gct gag att tcc ttg acc cca ctc gaa ttc gac ctc ctg ctg | Asn Gly Ala Glu Ile Ser Leu Thr Pro Leu Glu Phe Asp Leu Leu Leu | 145 150 155 160 | 1021 |
| gaa ctc gcc cgc aaa cca cag caa gta ttc acc cgt gaa gaa ttg ctg | | | 1069 |

-continued

```
                Glu Leu Ala Arg Lys Pro Gln Gln Val Phe Thr Arg Glu Leu Leu
                                165                 170                 175 ggc aaa gtg tgg ggc tac cgc cac gca tcc gac act cga ctg gtc aac        1117
Gly Lys Val Trp Gly Tyr Arg His Ala Ser Asp Thr Arg Leu Val Asn
            180                 185                 190 gtt cac gtt cag cgt ctg cgc gcc aag att gaa aaa gat cca gaa aat        1165
Val His Val Gln Arg Leu Arg Ala Lys Ile Glu Lys Asp Pro Glu Asn
        195                 200                 205 ccg cag atc gtc ctc acc gtc cgc ggt gtt ggc tac aaa act ggc cac        1213
Pro Gln Ile Val Leu Thr Val Arg Gly Val Gly Tyr Lys Thr Gly His
    210                 215                 220 aac gat taagtttttc atttaaaaaa ggggcagttt ctcattcttg cctggctcac         1269
Asn Asp
225 gcgacttcga catcgcattg tagataaatg gcgaacctca ctg cag gtt cgc gtg        1324
                                             Leu Gln Val Arg Val
                                                             230 ctc ggc tcc atc ttc acc gca tca gct gtc gtg atg atc ctt ttg ggg        1372
Leu Gly Ser Ile Phe Thr Ala Ser Ala Val Val Met Ile Leu Leu Gly
                235                 240                 245 ctg ggc atg ctg act gta ttc acc caa cgg ttg gtg gat cag aaa atc        1420
Leu Gly Met Leu Thr Val Phe Thr Gln Arg Leu Val Asp Gln Lys Ile
            250                 255                 260 gat att gcg agc tcc gaa atc gac cgc gcc cgc gtc atc gtc gaa gag        1468
Asp Ile Ala Ser Ser Glu Ile Asp Arg Ala Arg Val Ile Val Glu Glu
        265                 270                 275 caa atc acc gca tcc ggc gcc tca aca tcg gtg cag gcg cga gtg aac        1516
Gln Ile Thr Ala Ser Gly Ala Ser Thr Ser Val Gln Ala Arg Val Asn
    280                 285                 290                 295 tct gcc cgc gct gcg ctc tcc agc ttg ggt acc agc ggc ggt aca gaa        1564
Ser Ala Arg Ala Ala Leu Ser Ser Leu Gly Thr Ser Gly Gly Thr Glu
                300                 305                 310 acc aac gcc gcc tac gat cca gtc gtg ttg gtg aac aac gat gac ctg        1612
Thr Asn Ala Ala Tyr Asp Pro Val Val Leu Val Asn Asn Asp Asp Leu
            315                 320                 325 gtg gtc tct ccc gag ggt tac caa atc cca gaa cgt ctg cga tac ttc        1660
Val Val Ser Pro Glu Gly Tyr Gln Ile Pro Glu Arg Leu Arg Tyr Phe
        330                 335                 340 gtc tct gag aac caa gtc tcg tat cag ttc tcc agc atc gac caa ggc        1708
Val Ser Glu Asn Gln Val Ser Tyr Gln Phe Ser Ser Ile Asp Gln Gly
    345                 350                 355 gac gga tcg tcc tac caa gcg ctc atc atc gga acg ccc acg gaa agc        1756
Asp Gly Ser Ser Tyr Gln Ala Leu Ile Ile Gly Thr Pro Thr Glu Ser
360                 365                 370                 375 gac atc ccg aac ctc cag gtg tat ctg gtg ttc tcc atg gaa agc gac        1804
Asp Ile Pro Asn Leu Gln Val Tyr Leu Val Phe Ser Met Glu Ser Asp
                380                 385                 390 gaa tcc tct ctt gct ctc atg cga gga ctc ctc tca gct gca ctg ctg        1852
Glu Ser Ser Leu Ala Leu Met Arg Gly Leu Leu Ser Ala Ala Leu Leu
            395                 400                 405 atc gtg gtg gtg ctg ctg gtc ggt atc gca tgg cta gcc acc caa cag        1900
Ile Val Val Val Leu Leu Val Gly Ile Ala Trp Leu Ala Thr Gln Gln
        410                 415                 420 gtc acc gcg ccg gtg cgt tcg gcg agc cgg att gcg gag cgt ttc gct        1948
Val Thr Ala Pro Val Arg Ser Ala Ser Arg Ile Ala Glu Arg Phe Ala
    425                 430                 435 caa ggc aaa ctg cgt gaa cgc atg gtg gtg gaa ggc gaa gac gag atg        1996
Gln Gly Lys Leu Arg Glu Arg Met Val Val Glu Gly Glu Asp Glu Met
440                 445                 450                 455
```

```
                                                        -continued
gcc cgc ctg gcg gtg tcc ttc aac gcg atg gcc gaa tcg ctg tcc gcg    2044
Ala Arg Leu Ala Val Ser Phe Asn Ala Met Ala Glu Ser Leu Ser Ala
                460                 465                 470 cag atc acc aaa ttg gag gaa tac ggc aat ctg caa cga caa ttc aca    2092
Gln Ile Thr Lys Leu Glu Glu Tyr Gly Asn Leu Gln Arg Gln Phe Thr
            475                 480                 485 tcg gat gtc tca cac gaa ttg cgc aca ccg ctg aca acg gtg cgc atg    2140
Ser Asp Val Ser His Glu Leu Arg Thr Pro Leu Thr Thr Val Arg Met
        490                 495                 500 gct gct gat cta att gcc gat agt gaa gat gaa ctt tca ccc ggt gcg    2188
Ala Ala Asp Leu Ile Ala Asp Ser Glu Asp Glu Leu Ser Pro Gly Ala
    505                 510                 515 cgc cgc gcc agc caa ctg atg aac agg gag ttg gac cga ttc gag tcg    2236
Arg Arg Ala Ser Gln Leu Met Asn Arg Glu Leu Asp Arg Phe Glu Ser
520                 525                 530                 535 ctg ctg agc gat ctg ttg gaa att tcc cga cac gac gcc ggc gtt gcc    2284
Leu Leu Ser Asp Leu Leu Glu Ile Ser Arg His Asp Ala Gly Val Ala
                540                 545                 550 gaa ctg tcc acc gcg ctt cac gat gtc cgc atc cca gtg cga tcg gca    2332
Glu Leu Ser Thr Ala Leu His Asp Val Arg Ile Pro Val Arg Ser Ala
            555                 560                 565 ttg gaa caa gta caa cac ttg gcc acc gag ctc gat gtg gaa ttg ctt    2380
Leu Glu Gln Val Gln His Leu Ala Thr Glu Leu Asp Val Glu Leu Leu
        570                 575                 580 gtt aat ttg ccc gaa gaa gcg atc aac att caa ggc gat tcc agg cgc    2428
Val Asn Leu Pro Glu Glu Ala Ile Asn Ile Gln Gly Asp Ser Arg Arg
    585                 590                 595 atc gaa aga atc att cgc aac ctt cta gcc aat gcg atc gac cac tcc    2476
Ile Glu Arg Ile Ile Arg Asn Leu Leu Ala Asn Ala Ile Asp His Ser
600                 605                 610                 615 aag ggc ttg cct gtt gag ttg aaa gtt gcc gac aac gtg gac gca gta    2524
Lys Gly Leu Pro Val Glu Leu Lys Val Ala Asp Asn Val Asp Ala Val
                620                 625                 630 gcg atc gtt gtt att gat cac ggc gtc ggc ctg aaa cct gga caa gac    2572
Ala Ile Val Val Ile Asp His Gly Val Gly Leu Lys Pro Gly Gln Asp
            635                 640                 645 gaa ttg gtg ttc aac aga ttc tgg cga gcc gac cct tcg cgc gtc cgc    2620
Glu Leu Val Phe Asn Arg Phe Trp Arg Ala Asp Pro Ser Arg Val Arg
        650                 655                 660 cat tct ggt ggc acc ggc ctg ggt ctt gcg att tct cgc gaa gat gcg    2668
His Ser Gly Gly Thr Gly Leu Gly Leu Ala Ile Ser Arg Glu Asp Ala
    665                 670                 675 atg ctt cat gga gga aac ctt gat gcg gcg gga acg atc ggt gtt ggt    2716
Met Leu His Gly Gly Asn Leu Asp Ala Ala Gly Thr Ile Gly Val Gly
680                 685                 690                 695 tcc att ttc cgt ttg gtc ttg cct aaa gaa ccg cat gga aat tat cgt    2764
Ser Ile Phe Arg Leu Val Leu Pro Lys Glu Pro His Gly Asn Tyr Arg
                700                 705                 710 gaa gca ccg atc ccg ttg atc gct cca gag aca ccg tgg gaa ggg gag    2812
Glu Ala Pro Ile Pro Leu Ile Ala Pro Glu Thr Pro Trp Glu Gly Glu
            715                 720                 725
cag cag tgagtaaaat ttcgacgaaa ctgaaggccc tcaccgcggt gctgtctgtg    2868
Gln Gln accactctgg tggctgggtg ttccacgctt ccgcagaaca cggatccgca agtgctgcgc    2928
tcattttccg ggtcccaaag cacacaagag atagcagggc cgaccccgaa tcaagatccg    2988
gatttgttga tccgcggctt cttcagcgca ggtgcgtatc cgactcagca gtatgaagcg    3048
gcgaaggcgt atctgacgga agggacgcgc agcacgtgga atccggctgc gtcgactcgt    3108
attttggatc gcattgatct gaacactctg ccaggttcga cgaatgcgga acgaacgatt    3168
```

-continued

| | |
|---|---|
| gcgatccgtg gaacgcaggt cggaacgttg ctcagcggtg gcgtgtatca gccggagaat | 3228 |
| gcggagtttg aagctgagat cacgatgcgt cgggaagatt gggagtggcg tatcgatgct | 3288 |
| ttgccggacg ggatttattt agagagaaac gatctgcgga accattacac tccgcacgat | 3348 |
| gtgtatttct ttgatccttc tggccaggtg ttggtggggg atcggcgttg gttgttcaat | 3408 |
| gagtcgcagt cgatgtccac ggtgctgatg gcccttctgg ttaatggtcc ttcgccggca | 3468 |
| atttctcctg gtgtggtcaa tcagctgtcc acggatgcgt cgttcgtggg gttcaatgat | 3528 |
| ggggagtatc agttcactgg tttgggaaat tggatgatg atgcgcgttt gcgtttcgcc | 3588 |
| gcccaggccg tgtggacgtt ggcgcatgct gatgtcgcag gccctacac tttggtcgct | 3648 |
| gacggcgcgc cgttgctgtc ggagttccca acgctcacca ccgatgacct cgccgaatac | 3708 |
| aacccagagg cttacaccaa cacggtgtcc acgttgtttg cgttgcagga tggatcgttg | 3768 |
| tcgagggtca gttccggcaa tgtgagtcca ctacagggca tttggagcgg tggagatatc | 3828 |
| gattctgcag cgatttcctc ctccgccaat gtggtggcag cggtacgcca cgaaaacaac | 3888 |
| gaggcagtgc ttactgttgg ct | 3910 |

<210> SEQ ID NO 2
<211> LENGTH: 226
<212> TYPE: PRT
<213> ORGANISM: Corynebacterium glutamicum

<400> SEQUENCE: 2

```
Met Ser Gln Lys Ile Leu Val Val Asp Asp Pro Ala Ile Ser Glu
1               5                   10                  15

Met Leu Thr Ile Val Leu Ser Ala Glu Gly Phe Asp Thr Val Ala Val
            20                  25                  30

Thr Asp Gly Ala Leu Ala Val Glu Thr Ala Ser Arg Glu Gln Pro Asp
        35                  40                  45

Leu Ile Leu Leu Asp Leu Met Leu Pro Gly Met Asn Gly Ile Asp Ile
    50                  55                  60

Cys Arg Leu Ile Arg Gln Glu Ser Ser Val Pro Ile Ile Met Leu Thr
65                  70                  75                  80

Ala Lys Thr Asp Thr Val Asp Val Val Leu Gly Leu Glu Ser Gly Ala
                85                  90                  95

Asp Asp Tyr Val Asn Lys Pro Phe Lys Ala Lys Glu Leu Val Ala Arg
            100                 105                 110

Ile Arg Ala Arg Leu Arg Ala Thr Val Asp Glu Pro Ser Glu Ile Ile
        115                 120                 125

Glu Val Gly Asp Leu Ser Ile Asp Val Pro Ala His Thr Val Lys Arg
    130                 135                 140

Asn Gly Ala Glu Ile Ser Leu Thr Pro Leu Glu Phe Asp Leu Leu Leu
145                 150                 155                 160

Glu Leu Ala Arg Lys Pro Gln Gln Val Phe Thr Arg Glu Glu Leu Leu
                165                 170                 175

Gly Lys Val Trp Gly Tyr Arg His Ala Ser Asp Thr Arg Leu Val Asn
            180                 185                 190

Val His Val Gln Arg Leu Arg Ala Lys Ile Glu Lys Asp Pro Glu Asn
        195                 200                 205

Pro Gln Ile Val Leu Thr Val Arg Gly Val Gly Tyr Lys Thr Gly His
    210                 215                 220

Asn Asp
225
```

<210> SEQ ID NO 3
<211> LENGTH: 503
<212> TYPE: PRT
<213> ORGANISM: Corynebacterium glutamicum

<400> SEQUENCE: 3

Leu Gln Val Arg Val Leu Gly Ser Ile Phe Thr Ala Ser Ala Val Val
1               5                   10                  15

Met Ile Leu Leu Gly Leu Gly Met Leu Thr Val Phe Thr Gln Arg Leu
            20                  25                  30

Val Asp Gln Lys Ile Asp Ile Ala Ser Ser Glu Ile Asp Arg Ala Arg
        35                  40                  45

Val Ile Val Glu Glu Gln Ile Thr Ala Ser Gly Ala Ser Thr Ser Val
    50                  55                  60

Gln Ala Arg Val Asn Ser Ala Arg Ala Ala Leu Ser Ser Leu Gly Thr
65                  70                  75                  80

Ser Gly Gly Thr Glu Thr Asn Ala Ala Tyr Asp Pro Val Val Leu Val
                85                  90                  95

Asn Asn Asp Asp Leu Val Val Ser Pro Glu Gly Tyr Gln Ile Pro Glu
            100                 105                 110

Arg Leu Arg Tyr Phe Val Ser Glu Asn Gln Val Ser Tyr Gln Phe Ser
        115                 120                 125

Ser Ile Asp Gln Gly Asp Gly Ser Ser Tyr Gln Ala Leu Ile Ile Gly
    130                 135                 140

Thr Pro Thr Glu Ser Asp Ile Pro Asn Leu Gln Val Tyr Leu Val Phe
145                 150                 155                 160

Ser Met Glu Ser Asp Glu Ser Ser Leu Ala Leu Met Arg Gly Leu Leu
                165                 170                 175

Ser Ala Ala Leu Leu Ile Val Val Leu Leu Val Gly Ile Ala Trp
            180                 185                 190

Leu Ala Thr Gln Gln Val Thr Ala Pro Val Arg Ser Ala Ser Arg Ile
        195                 200                 205

Ala Glu Arg Phe Ala Gln Gly Lys Leu Arg Glu Arg Met Val Val Glu
    210                 215                 220

Gly Glu Asp Glu Met Ala Arg Leu Ala Val Ser Phe Asn Ala Met Ala
225                 230                 235                 240

Glu Ser Leu Ser Ala Gln Ile Thr Lys Leu Glu Glu Tyr Gly Asn Leu
                245                 250                 255

Gln Arg Gln Phe Thr Ser Asp Val Ser His Glu Leu Arg Thr Pro Leu
            260                 265                 270

Thr Thr Val Arg Met Ala Ala Asp Leu Ile Ala Asp Ser Glu Asp Glu
        275                 280                 285

Leu Ser Pro Gly Ala Arg Arg Ala Ser Gln Leu Met Asn Arg Glu Leu
    290                 295                 300

Asp Arg Phe Glu Ser Leu Leu Ser Asp Leu Leu Glu Ile Ser Arg His
305                 310                 315                 320

Asp Ala Gly Val Ala Glu Leu Ser Thr Ala Leu His Asp Val Arg Ile
                325                 330                 335

Pro Val Arg Ser Ala Leu Glu Gln Val Gln His Leu Ala Thr Glu Leu
            340                 345                 350

Asp Val Glu Leu Leu Val Asn Leu Pro Glu Glu Ala Ile Asn Ile Gln
        355                 360                 365

Gly Asp Ser Arg Arg Ile Glu Arg Ile Ile Arg Asn Leu Leu Ala Asn

```
                    370             375             380
Ala Ile Asp His Ser Lys Gly Leu Pro Val Glu Leu Lys Val Ala Asp
385             390             395             400

Asn Val Asp Ala Val Ala Ile Val Val Ile Asp His Gly Val Gly Leu
            405             410             415

Lys Pro Gly Gln Asp Glu Leu Val Phe Asn Arg Phe Trp Arg Ala Asp
            420             425             430

Pro Ser Arg Val Arg His Ser Gly Thr Gly Leu Gly Leu Ala Ile
            435             440             445

Ser Arg Glu Asp Ala Met Leu His Gly Gly Asn Leu Asp Ala Ala Gly
450             455             460

Thr Ile Gly Val Gly Ser Ile Phe Arg Leu Val Leu Pro Lys Glu Pro
465             470             475             480

His Gly Asn Tyr Arg Glu Ala Pro Ile Pro Leu Ile Ala Pro Glu Thr
            485             490             495

Pro Trp Glu Gly Glu Gln Gln
            500

<210> SEQ ID NO 4
<211> LENGTH: 20
<212> TYPE: DNA
<213> ORGANISM: Corynebacterium glutamicum

<400> SEQUENCE: 4
tgatgcttcc aggcatgaac                                              20

<210> SEQ ID NO 5
<211> LENGTH: 20
<212> TYPE: DNA
<213> ORGANISM: Corynebacterium glutamicum

<400> SEQUENCE: 5
gatcgccgac ttcgatgatt                                              20

<210> SEQ ID NO 6
<211> LENGTH: 20
<212> TYPE: DNA
<213> ORGANISM: Corynebacterium glutamicum

<400> SEQUENCE: 6
acgatgacct ggtggtctct                                              20

<210> SEQ ID NO 7
<211> LENGTH: 20
<212> TYPE: DNA
<213> ORGANISM: Corynebacterium glutamicum

<400> SEQUENCE: 7
gactcgaatc ggtccaactc                                              20
```